US005635444A

United States Patent [19]

Walker et al.

[11] Patent Number: 5,635,444
[45] Date of Patent: Jun. 3, 1997

[54] CONTROL OF CRABGRASS WITH A FUNGAL PATHOGEN

[76] Inventors: Harrell L. Walker, Rte. 1, Box 2070-4, Ruston, La. 71270; Anthony M. Tilley, Rte. 4, Box 262, Minden, La. 71055

[21] Appl. No.: 234,264

[22] Filed: Apr. 28, 1994

[51] Int. Cl.$^6$ .................................................. A01N 63/04
[52] U.S. Cl. ....................................................... 504/117
[58] Field of Search ............................................. 504/117

[56] References Cited

U.S. PATENT DOCUMENTS

| | | | |
|---|---|---|---|
| 4,390,360 | 6/1983 | Walker | 71/79 |
| 4,419,120 | 12/1983 | Swalker | 71/79 |
| 4,715,881 | 12/1987 | Anderson | 71/79 |
| 4,718,935 | 1/1988 | Walker | 71/79 |
| 4,724,147 | 2/1988 | Marios | 424/93 |
| 4,767,441 | 8/1988 | Walker | 71/79 |
| 4,818,530 | 4/1989 | Marios | 424/93 |
| 5,192,541 | 3/1993 | Savage | 424/93 |

*Primary Examiner*—Brian M. Burn
*Assistant Examiner*—Brian G. Bembenick
*Attorney, Agent, or Firm*—Joan M. Harrison

[57] ABSTRACT

A method for biological control of pest grasses such as crabgrass using two species of a fungus selected from the genus Curvularia. The fungus is applied to the grass in amounts effective to produce typical plant lesions which kill or suppress, and thus control, the grass. The fungus may be administered with a surfactant or as granules, either of which may include additives such as glucose to enhance the pathogenic action of the fungus. Two species of the fungus are on deposit with the Department of Biological Sciences, Louisiana Tech University in Ruston, La. and with the International Mycological Institute in Surrey, UK and have been assigned the numbers MT-5 and CG-L.

10 Claims, 1 Drawing Sheet

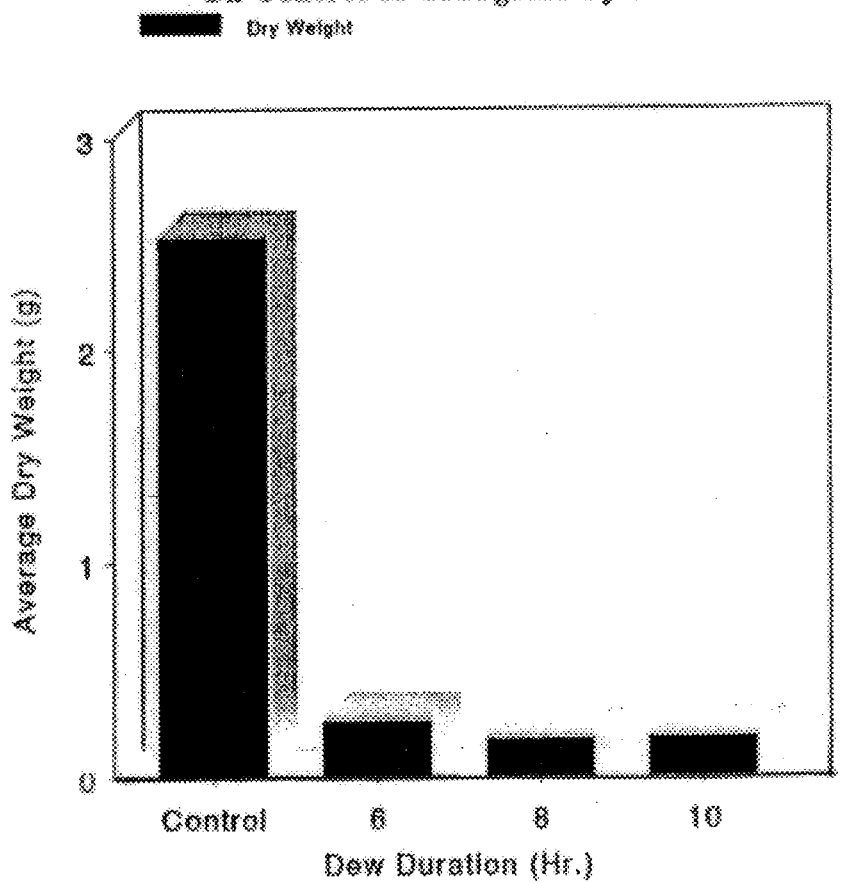
Effect of dew duration on kill of crabgrass plants by MT-5. Control received surfactant only followed by a 10 hr. dew period. Data are averages of 4 replications.

CONTROL OF CRABGRASS WITH A FUNGAL PATHOGEN

BACKGROUND OF THE INVENTION

1. Field of the Invention

This invention relates to bioherbicides for controlling pest plants such as weeds and more particularly, to a method for biological control of a variety of pest plants including crabgrass using two species of a fungus selected from the genus Curvularia. Typically, a selected concentration of conidia in a liquid surfactant such as nonoxynol is applied to the pest plants to produce typical lesions which kill or suppress, and thus control, the plants. Alternatively, the conidia may be applied to the plants using an organosilicone surfactant such as Silwet L-77 (trademark), which has been found to enhance the pathogenic action of Curvularia. Granular preparations of the fungus are suitable for preemergence or postemergence application. Curvularia may be applied to crops in combination with the fungus Alternaria cassiae to control a broader range of pest plants than is achieved using either fungus alone.

Weeds present a tremendous problem to farmers throughout the world, causing an estimated 10–12% loss of value for agricultural products in the United States, the most recent estimate being $20 billion annually (McWhorter, C. G. [1984] Weed Science, 32:850–855). Chemical pesticides are commonly used to control pest grasses in agricultural crops, but concern over environmental damage caused by these pesticides has recently elicited societal pressures to replace the chemical pesticides with alternative control methods. One area of active research in this area involves the use of plant pathogens, including both bacteria and fungi, to attack and kill pest plants in agricultural crops.

A major constraint to commercial development of a plant pathogan as a biological herbicide is selectivity. A pathogen that controls only one weed species in one type of crop does not have the same market potential as a pathogen that controls several important weed species in different types of crops. It has surprisingly been found that two fungus species of the genus Curvularia are effective in controlling multiple varieties of pest grasses in several different types of important agricultural crops. In addition to controlling crabgrass species, the fungi utilized in this invention are effective in controlling barnyard grass, green foxtail and other susceptible pest grasses, but do not harm sugar cane or broadleafed crop plants such as soybean, cotton and peanuts. Since Bermuda grass, St. Augustine grass, Centipede grass and Zoysia grass are also unharmed by the fungus, Curvularia may also be used to control weed growth in residential and commercial yards. In addition to the pest grasses mentioned above, sicklepod may also be controlled by using the fungus Alternaria cassiae Curvularia in combination with Curvularia.

2. Description of the Prior Art

Several methods are known in the art for using biological organisms to control weeds and other pest plants. As disclosed in U.S. Pat. No. 3,999,973, to Daniel, et al, the anthracnose fungus Coltetotrichum gloeosporioides has been used to control the weed northern jointvetch and another strain of this fungus has been used to control winged waterprimrose. Colletotrichum malvarum has been used to control prickly sida. These three pathogens have been combined to control all three target weeds at once. In other experimental work the fungus Alternaria macrospora has been used to control spurred anoda (Anoda cristata), Weed Science, H. L. Walker, 1981, Vol. 29, pp.505–507.

My U.S. Pat. No. 4,390,360, dated Jun. 28, 1983, describes "Control of Sicklepod, Showy Crotalaria and Coffee Senna With A Fungal Pathogen" using a specific host strain of the fungus Alternaria cassiae to produce typical weed lesions which kill or suppress the respective weeds. My U.S. Pat. No. 4,419,120, dated Dec. 6, 1983, discloses "Control of Prickly Sida, Velvetleaf and Spurred Anoda With Fungal Pathogens" using a specific host strain of the fungus Fusarium lateritium to kill or suppress the respective weeds. U.S. Pat. No. 4,715,881, dated Dec. 29, 1987, to Andersen, et al, details "Control of Eastern Black Nightshade With a Fungal Pathogen" using a strain of Colletotrichum coccodes which is selectively pathogenic toward eastern black nightshade (Solanum ptycanthum). My U.S. Pat. No. 4,718,935, dated Jan. 12, 1988 and U.S. Pat. No. 4,767,441, dated Aug. 30, 1988, describe a "Method For The Preparation of Mycoherbicide-Containing Pellets" characterized by alginate gel pellets containing living fungus capable of producing conidia when exposed to sufficient light and moisture. U.S. Pat. No. 4,724,147, dated Feb. 9, 1988, to James J. Marois, et al, and U.S. Pat. No. 4,818,530, dated Apr. 4, 1989, also to James J. Marois, et al, both detail the "Preparation of Pellets Containing Fungi for Control of Soilborne Diseases", in which fungi are first selected and grown for a time sufficient to produce inoculum. The fungal propagules are harvested, homogenized and diluted with sodium alginate solution. Pelletization is then accomplished by dropwise addition of the fungal propagule-alginate mixture into a solution of calcium chloride or calcium gluconate. The resulting alginate gel pellets containing living fungi can then be dried and used to inoculate agricultural fields infested with soilborne plant diseases. U.S. Pat. No. 5,192,541, dated Mar. 9, 1993, to Steven D. Savage, et al, describes "Weed-Killing Xanthomonas campestris", in which novel microorganisms useful in controlling unwanted grasses and other weeds are discovered through a unique process which involves isolating plant pathogens from asymptomatic plants.

SUMMARY OF THE INVENTION

The present invention is directed to a method for biological control of a variety of pest grasses including crabgrass, barnyard grass, green foxtail and other susceptible grasses using two species of a fungus selected from the genus Curvularia. The fungus is isolated from diseased plants and conidia are produced using incubation on Petri dish cultures or a two-stage process involving submerged liquid fermentation and tray culture. Inoculum is produced by harvesting conidia from the Petri dishes using a surfactant in distilled water or by pelletization of the mycelial homogenate resulting from the submerged liquid fermentation process. Curvularia may be applied to agricultural crops in combination with Alternaria cassiae to control a broader range of pest plants than is achieved using either fungus alone.

BRIEF DESCRIPTION OF THE DRAWINGS

The FIGURE illustrates the effect of dew duration on kill of crabgrass plants by Curvularia MT-5.

DESCRIPTION OF THE PREFERRED EMBODIMENTS

Two species of the fungus Curvularia are on deposit with the Department of Biological Sciences, Louisiana Tech University in Ruston, La. and with the International Mycological Institute in Surrey, UK, and have been assigned the numbers MT-5 and CG-L. The address of the Department of Biological Sciences is: Louisiana Tech University, Harrell L. Walker, Department of Biological Sciences, P.O. Box 3179, TS., Ruston, La. 71272.

The accession number for the deposit of the Curvularia MT-5 strain is IMI 361688. The accession number for the Curvularia CG-L strain is IMI 361689. The date of deposit of the Curvularia MT-5 strain is May 1, 1994. The date of deposit of the Curvularia CG-L deposit is May 1, 1994. The Curvularia MT-5 and the Curvularia CG-L strains are both identified as members of the Cochliobolus genus and the *intermedius* species thereof as identified by R. R. Nelson. The Curvularia MT-5 and CG-1 strains are both deposited at the International Mycological Institute located at Bakeham Lane, Egham, Surrey TW20 9TY, U.K.

The strains of Curvularia used in this invention were isolated from diseased plants of crabgrass (Diqitaria sp.) collected from various locations in Louisiana. Both the MT-5 strain and CG-L strain of Curvularia were isolated on potato dextrose agar (PDA), then subcultured on vegetable juice agar. The fungus sporulated profusely on vegetable juice agar in plastic Petri dishes incubated inverted at 24 C. with 12 hour photoperiods under two, 20-watt cool-white fluorescent lights directed upwardly from 20 cm. below the cultures. Conidia were harvested from the Petri dishes for foliar application using 0.02% surfactant in distilled water.

Mycelia of Curvularia were produced in submerged liquid culture by inoculation of cornmeal-soyflour-sucrose medium with conidia from cultures grown on vegetable juice agar in Petri dishes. The harvested mycelia were homogenized and induced to sporulate in pans by 12-hour photoperiods under 20-watt cool-white fluorescent lights suspended 40 cm above the pans. Conidia were harvested from the surface of the air-dried mycelia and then dried over $CaCl_2$ for 48 hours and stored at 4 C. Inoculum for foliar application was prepared by suspending the resulting dried spore preparations, which consisted of a wettable powder, in 0.02% surfactant.

Pellets of Curvularia MT-5 were prepared by adding sodium alginate to mycelial homogenate from submerged liquid culture and dripping the resulting mixture into 0.25M $CaCl_2$. The pathogen was easily recovered from the resulting pellets after air-drying the pellets. When the pellets were subsequently moistened and exposed to light as previously described, the MT-5 Curvularia sporulated profusely on the surfaces of the pellets, which were suitable for storage of the pathogen or use as a granular formulation for pre-emergence or post-emergence application.

Curvularia MT-5 exhibited a relatively broad host range. Crabgrass was consistently killed or suppressed by the pathogen and proved to be the species most susceptible. Other species that were also susceptible included green foxtail (Setaria sp.), barnyard grass (Echinochloa sp.) and shattercane (Sorghum sp.). Species that were resistant or immune included soybeans, cotton, sugar cane, Zoysia grass, Bermuda grass, Centipede grass and St. Augustine grass. Because Curvularia MT-5 is effective in controlling a variety of pest grasses and does not harm important crops and grasses, the fungus has exhibited great potential as a bioherbicide.

Curvularia CG-L was not included in the host range tests of these studies. However, crabgrass was consistently killed or suppressed and both cotton and soybeans were unharmed when Curvularia CG-L was applied to cotton and crabgrass plants growing together in pots or soybeans and crabgrass plants growing together. Both crabgrass and sicklepod were consistently killed or suppressed and soybeans were unharmed when Curvularia CG-L and *Alternaria cassiae* were applied in combination in tests containing crabgrass, sicklepod and soybeans growing together in pots.

The following examples illustrate application of the Curvularia fungus MT-5:

EXAMPLE 1

Pathogen Isolation and Culture

Diseased plants of crabgrass (Diqitaria sp.) were collected from various locations in Louisiana. The MT-5 strain of Curvularia was isolated from pieces of the diseased plants that were plated on Petri dishes containing potato dextrose agar (PDA) supplemented with streptomycin sulfate (6.25 g/L) and chloramphenicol (3.75 g/L). The cultures were inverted and incubated at 24 C, with 12 hour photoperiods. Light was provided by two 20-watt cool-white fluorescent lights that were directed upwardly from 20 cm. below the cultures. As Curvularia MT-5 grew from the diseased tissue, the fungus was transferred to Petri dishes containing PDA or vegetable juice agar. The pathogen produced conidia on both media, but conidia were more abundant for cultures grown on vegetable juice agar.

Conidia were also produced using a two-stage fermentation process that has been described for other fungi. Mycelia were produced in submerged liquid culture by inoculation of cornmeal-soyflour-sucrose medium with conidia from cultures grown on vegetable juice agar. The mycelia were harvested from the liquid culture, homogenized in a Waring Blendor and poured into pans (435×275 cm). Each pan received 300 ml of homogenized mycelia, which were induced to sporulate by 12 hour photoperiods provided by 20-watt cool-white fluorescent lights suspended 40 cm above the pans. After 48 to 72 hours, the conidia and mycelia were air-dried and the conidia were harvested from the surface of the mycelia using a cyclone collector. The conidia were dried over $CaCl_2$ for 48 hours and stored at 4 C. These dried conidial preparations typically contained approximately $4 \times 10^8$ conidia per gram as determined with a hemacytometer.

Pellets of Curvularia MT-5 were prepared by adding sodium alginate (1% final concentration of Kelgin MV) to mycelial homogenate from submerged liquid culture and dripping this mixture into 0.25M $CaCl_2$. The pathogen could be easily recovered from air-dried pellets. When the dried pellets were moistened and exposed to light as previously described, the Curvularia MT-5 sporulated profusely on the surfaces of the pellets. These pellets were suitable for storage of the pathogen or for use as granular formulations for preemergence or postemergence application.

EXAMPLE 2

Host Range Tests

Host range tests of Curvularia MT-5 were conducted in a greenhouse at Louisiana Tech University. Seedlings of test plants were grown in a commercially-prepared blend of peat, vermiculite and fertilizer. The size of the containers used varied from 5.5 cm square to 15 cm round, depending on the species of plants and the duration of the experiments. Inoculum for greenhouse tests was produced in Petri dishes of vegetable juice agar, as described in Example 1. Conidia were harvested using 0.02% (v/v) surfactant, nonoxynol (9 to 10 POE) [a(p-nonylphenyl)-w-hydroxypoly) oxyethylene)] in distilled water. Inoculum for some tests consisted of dried spore preparations (a wettable powder)

suspended in 0.02% surfactant. Inoculum containing $1 \times 10^5$ conidia/ml was sprayed to near runoff onto test seedlings that were 7 to 10 days old. Control plants were sprayed with water and 0.02% surfactant only. All plants were placed in dew chambers for 10–18 hours, then moved to a greenhouse bench and observed 14 days for disease development. Susceptible plants exhibited necrotic spots and kill of leaves or plants. Crabgrass was consistently killed or suppressed by the pathogen and was the species most susceptible in these tests. Kill of crabgrass seedlings consistently approached 90–100% within 48 hours after inoculation. Other species that were also susceptible included green foxtail (Setaria sp.), barnyard grass (Echinochloa sp.) and shattercane (Sorghum sp.). Control of these species ranged from 60% to 80%. Species that were resistant or immune included soybeans, cotton, sugar cane, Zoysia grass, Bermuda grass, Centipede grass and St. Augustine grass.

EXAMPLE 3

Selective Removal of Crabgrass from Soybeans Using Curvularia MT-5

Crabgrass and soybean (Cajun) seedlings were grown together in the same pots according to the conditions described in Example 2. Using the procedure of Example 2, crabgrass was consistently controlled (90–100%) with no damage to the soybeans resulting.

EXAMPLE 4

Enhanced Activity of Curvularia MT-5 With Organosilicone Surfactant

The procedure of Example 3 was repeated, except an organosilicone surfactant [Silwet L-77 (trademark), 0.05% (V/V) in distilled water] was substituted for nonoxynol and cotton (Stoneville 453) was substituted for soybeans. Dew periods as short as 6 hours controlled 90–100% of crabgrass growing in cotton, with no damage to the cotton resulting. Use of the organosilicone surfactant resulted in a significant increase in activity when compared to results obtained using nonoxynol. All crabgrass tissue was harvested 18 days after inoculation and dried at 75 C for 19 days. The FIGURE illustrates the effect of dew duration on kill of crabgrass plants by Curvularia MT-5.

EXAMPLE 5

The procedure of Example 4 was repeated except that soybeans were substituted for cotton. Dew periods as short as 6 hours controlled 90–100% of crabgrass with no damage to the soybeans resulting. Dew periods exceeding 10 hours resulted in minor phytotoxic injury to the soybeans.

The following examples illustrate application of the Curvularia fungus CG-L:

EXAMPLE 6

Selective Removal of Crabgrass From Soybeans Using Curvularia CG-L

Crabgrass and soybean (Cajun) seedlings were grown together in the same pots according to the conditions described in Example 2. Inoculum of Curvularia CG-L was prepared and applied to the crabgrass and soybean seedlings using the procedure of Example 2. Crabgrass was consistently controlled (90–100%) with no damage to the soybeans resulting.

EXAMPLE 7

Selective Removal of Crabgrass From Cotton Using Curvularia CG-L

Crabgrass and cotton seedlings were grown together in the same pots according to the conditions described in Example 2. Inoculum of Curvutaria CG-L was prepared and applied to the crabgrass and cotton seedlings using the procedure of Example 2. Crabgrass was consistently controlled (90–100%) with no damage to the cotton resulting.

EXAMPLE 8

Selective Removal of Crabgrass and Sicklepod From Soybeans Using A Combination of Curvularia CG-L and *Alternaria cassiae*

Crabgrass, sicklepod and soybean (Cajun) seedlings were grown together in the same pots according to the conditions described in Example 2. Inoculum of Curvularia CG-L and the fungus *Alternaria cassiae* were prepared and applied in combination to the crabgrass, sicklepod and soybean seedlings using the procedure of Example 2. Both crabgrass and sicklepod were consistently controlled (90–100%) with no damage to the soybeans resulting.

It is understood that various additives such as glucose may be added to the inoculum preparations of Curvularia MT-5 or Curvularia CG-L to enhance the pathogenic action of the respective pathogen. Inoculum preparations of Curvularia MT-5 and Curvularia CG-L may be applied to the pest plants in combination to enhance the pathogenic action of each fungus. Granular application of Curvularia is not limited to the use of alginate gel pellets, but may alternatively include granules which consist of the fungus and a carrier such as vermiculite, corn cob grits or clay. Some or all of the pathogenic properties of a fungus may be attributed to toxins or metabolites released by the fungus into the host plant. Accordingly, isolation of heretofore unidentified pathogenic substances secreted by Curvularia MT-5 or Curvularia CG-L and application of the substances to the host plants mentioned in these studies may prove to be an effective method in controlling the plants.

Accordingly, it is understood that the Curvularia fungus can be used effectively to control crabgrass and other susceptible grasses in a number of different environments including vegetable gardens, lawns and turf, field crops and the like, in non-exclusive particular.

Having described my invention with the particularity set forth above, I claim:

1. A method for controlling plant weeds of crabgrass, barnyard grass, green foxtail, shattercane and other susceptible grasses, comprising inoculating a field with at least one fungus selected from the group consisting of Curvularia MT-5 and Curvularia CG-L in an amount effective to control said plant weeds.

2. The method of claim 1 wherein said fungus is applied to the field as a foliar spray.

3. The method of claim 1 wherein said fungus is applied to the field as granules that consist of the fungus and an inert carrier.

4. The method of claim 1 wherein said fungus is applied to the field as granules that consist of the fungus and an alginate gel pellet.

5. The method of claim 1 wherein said fungus is applied to the field as a wettable powder.

6. A method for controlling plant weeds of crabgrass, barnyard grass, green foxtail, shattercane, other susceptible grasses and sicklepod, comprising inoculating a field with a combination of the fungus *Alternaria cassiae* and at least one fungus selected from the group consisting of Curvularia MT-5 and Curvularia CG-L in an amount effective to control said plant weeds.

7. The method of claim 6 wherein said fungus is applied to the field as a foliar spray.

8. The method of claim 6 wherein said fungus is applied to the field as granules that consist of the fungus and an inert carrier.

9. The method of claim 6 wherein said fungus is applied to the field as granules that consist of the fungus and an alginate gel pellet.

10. The method of claim 6 wherein said fungus is applied to the field as a wettable powder.

* * * * *